United States Patent
Fruehauf et al.

(12)
(10) Patent No.: US 6,261,795 B1
(45) Date of Patent: *Jul. 17, 2001

(54) RADIATION RESISTANCE ASSAY FOR PREDICTING TREATMENT RESPONSE AND CLINICAL OUTCOME

(75) Inventors: John P. Fruehauf, Tustin; Ricardo J. Parker, Mission Viejo, both of CA (US)

(73) Assignee: Oncotech, Inc., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/312,936

(22) Filed: May 17, 1999

Related U.S. Application Data

(63) Continuation of application No. 08/791,886, filed on Jan. 31, 1997, now Pat. No. 6,008,007.

(51) Int. Cl.⁷ .................. C12Q 1/02; C12Q 1/68

(52) U.S. Cl. .................................... 435/29; 435/6
(58) Field of Search ...................... 435/6, 29, 7.21

(56) References Cited

U.S. PATENT DOCUMENTS 6,008,007 * 12/1999 Fruehauf et al. .................. 435/29

* cited by examiner

*Primary Examiner*—Eggerton A. Campbell
(74) *Attorney, Agent, or Firm*—Morrison & Foerster LLP

(57) ABSTRACT

The present invention provides a novel method for assaying radiation resistance of cancer cells by isolating cancer cells, irradiating the cells, incubating the cells with a labeled marker indicative of cell proliferation, measuring the amount of labeled marker incorporated into the cells in order to determine the effect of radiation on the proliferation of cells, and then determining the relative resistance of the cells to radiation. Also provided are methods of assaying radiation resistance of cancer cells which are exposed to radiation and radio-sensitizing or chemotherapeutic agents.

2 Claims, 4 Drawing Sheets

RADIATION RESISTANCE ASSAY FOR PREDICTING TREATMENT RESPONSE AND CLINICAL OUTCOME

CROSS-REFERENCE TO RELATED APPLICATIONS

This application is a continuation of U.S. Pat. application Ser. No. 08/791,886, filed Jan. 31, 1997, now U.S. Pat. No. 6,008,007, the disclosure of which is herein incorporated by reference.

FIELD OF THE INVENTION

The present invention is in the field of radiation treatment for cancer. More particularly, the present invention describes a novel radiation resistance assay which quickly and reliably predicts patient outcome and response to radiation treatment of tumors. The novel assay can be used in conjunction with other radio-sensitive or chemotherapeutic agents to assay synergistic effects and to determine an effective course of treatment.

BACKGROUND

Radiation therapy is commonly used to treat various forms of cancers, either alone or in combination with chemotherapeutic agents. However, the effectiveness of radiation therapy varies depending on the nature of the cancer, the individual patient and whether radiation is used in combination with other treatments. Lokeshwar et al (1995) *Anticancer Res.* 15(1):93–98. For example, Hennequin et al. (1996) *Cancer Res.* 56(8):1842–50 have shown that chemical agents such as paclitaxel (Taxol) or docetaxel (Taxotere) can either reduce or enhance radiation sensitivity of cancer cell lines depending on the drug concentration. Edelstein et al. (1996) *Semin. Oncol.* 23(2 Suppl. 5):41–7 report that the chemotherapeutic agent vinorelbine can be used to potentiate the antitumor effects of radiation in cycling cells. Where cancers develop resistance to chemotherapeutic agents, Siler et al. (1996) *Cancer* 77(9):1850–1853 report that successful clinical outcomes may be obtained by combining chemotherapy with external beam radiation. Thus, it would be useful to have a fast, reliable in vitro assay which could accurately predict an individual's response to radiation treatment and the effect of radiation in combination with other chemotherapeutic or radiation-sensitizing agents.

In cervical cancer, for instance, the majority of patients are diagnosed with early stage disease. Among 13,458 staged patients with cervical carcinoma registered by the Surveillance, Epidemiology and End Results (SEER) program between 1973 and 1987, 71% were diagnosed with the International Federation of Gynecology and Obstetrics (FIGO) stage I–IIA tumors. However, patients with more advanced lesions accounted for the majority of cervical cancer deaths during the same time period (Kosary (1994) *Surgical Oncology,* 10:31–46). These deaths occurred despite current radiotherapy protocols, often as a direct result of clinical treatment failure. Indeed, the 1973 and 1978 Patterns of Care Studies reported the 4-year in-field treatment failure rates to range from 20% in women with stage IIB cancers to 47% in those with stage IIIB lesions. In these studies, FIGO stage and laterality of disease were the only significant pre-treatment predictors of in-field control and survival (Lanciano et al. (1991) *International J. Radiation Oncology,* 20:667–76). The most current FIGO staging for cervical cancer is shown in Table 1.

TABLE 1

| Stage | Description/Features |
|---|---|
| 0 | Carcinoma in situ, intraepithelial carcinoma (cases of stage 0 should not be included in any therapeutic statistics for invasive carcinoma) |
| I | Carcinoma strictly confined to the cervix; extension to the corpus should be disregarded<br>a. Preclinical carcinomas of the cervix; that is, those diagnosed only by microscopy<br>   Ia1. Minimal microscopically evident stromal invasion<br>   Ia2. Lesions detected microscopically that can be measured; the upper limit of the measurement should not show a depth of invasion of more than 5 mm taken from the base of the epithelium, either surface or glandular, from which it originates, and a second dimension, the horizontal spread must not exceed 7 mm; larger lesions should be staged as Ib<br>   Ib. Lesions of greater dimension than stage Ia2, whether seen clinically or not; space involvement should not alter the staging, but should be specifically recorded so as to determine whether it should affect treatment decisions in the future |
| II | Carcinoma extending beyond the cervix, but not onto the pelvic wall; involves the vagina, but not the lower one-third<br>a. No obvious parametrial involvement<br>b. Obvious parametrial involvement |
| III | Carcinoma extending onto the pelvic wall; (on rectal examination, there is no cancer-free space between the tumor and the pelvic wall; the tumor involves the lower one-third of the vagina; all cases with a hydronephrosis or nonfunctioning kidney)<br>a. No extension onto the pelvic wall<br>b. Extension onto the pelvic wall; urinary obstruction of one or both ureters on intravenous pyelogram (IVP) without the other criteria for stage III disease |
| IV | Carcinoma extending beyond the true pelvis or clinically involving the mucosa of bladder or rectum (a bullous edema, as such, does not permit a case to be allotted to stage IV)<br>a. Spread to adjacent organs<br>b. Spread to distant organs |

Presumably, control of tumors in the pelvic region in patients with advanced cervical cancer depends not only on stage and tumor volume but also on intrinsic biologic radiation sensitivity. Studies assessing the intrinsic radiation sensitivity of various cancer cell lines are known in the art Ruka et al. (1996) *J. Surg. Oncol.* 61(4):290–294 report that human soft tissue sarcoma cell lines do not show unusual radiation resistance when compared to human breast carcinomas or glioblastoma cell lines. Ma et al (1996) *Cell Biol. Int.* 20(4):289–292 describe how human diploid skin fibroblast cells exhibit heterogeneity in their response to radiation. None of these studies, however, indicate how in vitro radiation sensitivity could be used to predict clinical outcome.

To date, several trials investigating the utility of concomitant chemotherapy to improve radiation sensitivity have been inconclusive or have indicated that in vitro sensitivity is not predictive of clinical outcome. Ramsay et al. (1994) *Int. J. Radiation Oncology,* 31(2):339–344 describe how a tetrazolium-based colorimetric assay (MTT) is not a useful predictor of radiosensitivity of lymphocytes derived from breast cancer patients. Similarly, Taghian et al. (1995) *Int. J. Radiat. Oncol. Biol. Phys.* 32(1):99–104, report that in vitro radiation sensitivity of human glioblastoma, squamous cell carcinoma, soft tissue sarcoma and cancer colon samples does not correlate with either in vivo radiation sensitivity or clinical outcome.

Immunohistochemical in vitro assays have also shown no correlation between the expression of genes involved in cancer and radiation response. Zaffaroni et al. (1995) *Stem Cells* 13:77–85 report that p53 expression does not correlate with in vitro response to gamma irradiation in primary cultures of human ovarian cancers and cutaneous melanomas. Bristow et al. (1996) *Int. J. Radiat. Oncol. Biol. Phys.* 34(2):341–355 also found no relationship between radiation resistance and metastatic potential in cells transfected with the p53 gene.

Another assay described by Griffon et al. (1995) *European J. Cancer* 31A(1):85–91, uses a multicellular tumor spheroid (MTS) three-dimensional model to determine radiosensitivity. MTS cultures exhibit characteristic phenotypes, including having a spheroid, three-dimensional shape. Griffon measured the doubling time and DNA ploidy of MTS in response to radiation treatments. Notably, this study does not indicate if radiosensitivity in vitro is predictive of clinical outcome. In addition, the assay described by Griffon is both labor and time intensive. Although established tumor cell lines often produce MTS, primary tumor specimens do so only occasionally. Furthermore, the specimens obtained from patients must be grown for 4 to 5 days to develop spheroids which can be exposed to radiation. After radiation, the MTS must be cultured for at least 7 days before radiosensitivity can be measured. Thus, even if an MTS culture can be established from a patient sample, radiation response results are not available for a minimum of 11 days.

Chromosomal painting methods have also been used to try and predict radiation sensitivity. Dunst et al. (1995) *Strahlenther Onkol.* 171(10):581–586 describe how patients with abnormal and extreme radiosensitivity could possibly be identified by in-vitro testing of lymphocytes. Radiation sensitivity was determined by the amount of chromosomal damage, as measured by fluorescence in-situ hybridization (FISH). The assay described in Dunst is not predictive of clinical outcome in patients having decreased or normal radiosensitivity.

Clonogenic proliferation inhibition assays on fresh tumor explants have been the mainstay of in vitro radiation and chemotherapy response determination and have demonstrated prognostic value in human solid tumor models. C. M. West et al. (1993) *British J. Cancer,* 68:819–23 recently reported that patients with cervical carcinoma treated with radiotherapy alone and followed for a minimum of two years showed a correlation between in vitro response and clinical outcome. Life table analysis demonstrated a significantly longer disease-free survival in patients whose tumors were found to have higher than average in vitro response to radiation exposure. However, clonogenic assays have not been routinely incorporated in clinical trials due to several disadvantages, such as labor intensiveness, high cost, poor standardization due to low plating efficiencies and clump artifact, and long assay duration.

With the advent of in vitro $^3$H-Thymidine incorporation assays, several limitations of clonogenic techniques have been overcome. Specifically, $^3$H-Thymidine incorporation assays eliminate clump artifact, render reliable results in 85% of tumor explants examined, and can be completed within 6 days. While a variety of in vitro endpoints have been associated with radiation and chemotherapeutic drug response, proliferation inhibition assays have demonstrated the greatest clinical utility. This utility is based principally upon their high degree of accuracy at predicting resistance to chemotherapy. One such in vitro drug response assay, the Extreme Drug Resistance (EDR) assay, is currently being investigated by the Gynecologic Oncology Group (GOG) for its ability to predict clinical drug resistance and disease-free survival in patients undergoing primary chemotherapy for epithelial ovarian cancer. (see, Manetta et al. (ongoing) Protocol GOG #118). The EDR assay is a proliferation inhibition assay based on $^3$H-Thymidine incorporation by tumor cells grown in soft agar. In all solid tumor models studied thus far, results of the EDR assay have correlated with those of the clonogenic stem cell assay (Fruehauf *et al.,* "*In vitro* determination of drug response: A discussion of clinical applications "*Principles & Practice of Oncology. PPO Updates* (1993) 7(12):1–16).

There remains a need, however, for an assay which could confidently predict radiation resistance. The assay could predict local treatment failure with such combination regimens and could identify patients for whom unnecessary toxicity could be prevented and alternative therapies considered. Applicants describe herein a novel assay that can predict radiosensitivity of cancer cells, clinical resistance to primary radiation, interactions between chemotherapy and radiation, and clinical outcome.

SUMMARY OF THE INVENTION

The present invention provides a novel method for assaying radiation resistance of cancer cells by isolating cancer cells, irradiating the cells, incubating the cells with a labeled marker indicative of cell proliferation, measuring the amount of labeled marker incorporated into the cells in order to determine the effect of radiation on the proliferation of cells, and then determining the relative resistance of the cells to radiation. Also provided are methods of assaying radiation resistance of cancer cells which are exposed to radiation and radio-sensitizing or chemotherapeutic agents.

DETAILED DESCRIPTION OF THE INVENTION

Figure 1:
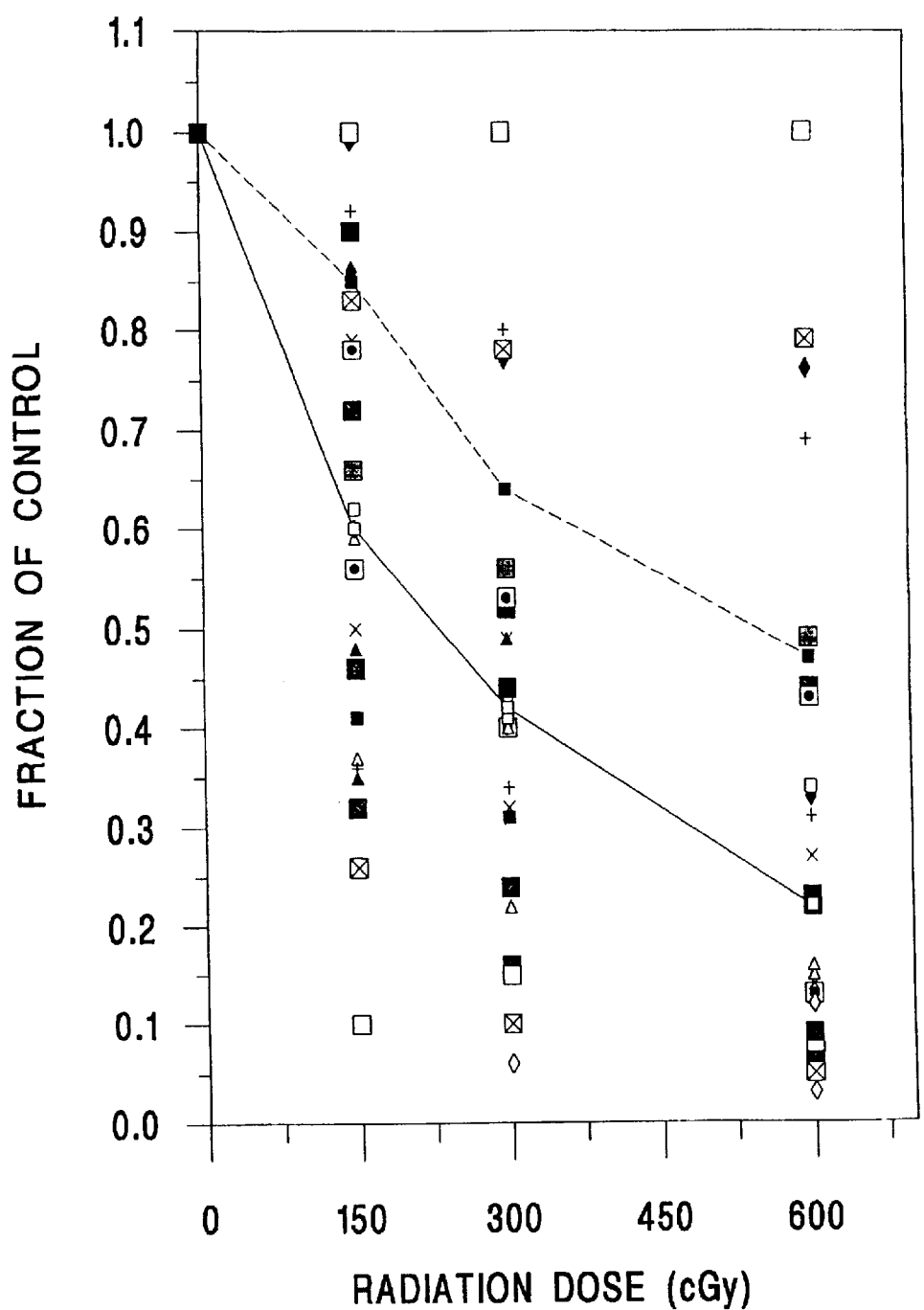
FIG. 1 shows the dose response curves of 26 cervical carcinomas based on defined drug resistance categories. The bottom solid line is the median dose and the top broken line is the median dose plus one standard deviation. Tumors with dose response curves below the median are considered to be more sensitive to radiation and, therefore, demonstrate Low Drug Resistance (LDR), whereas tumors with dose response curves above the median plus one standard deviation demonstrate Extreme Drug Resistance (EDR). Tumors with dose response curves between these two parameters demonstrate Intermediate Drug Resistance (IDR).
Figure 2A:
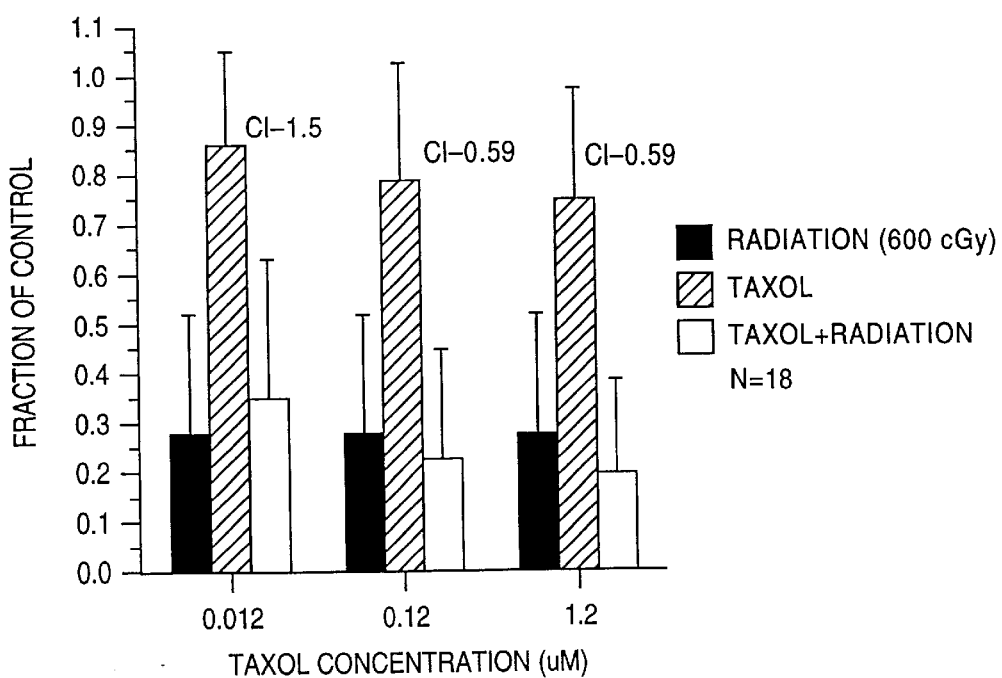
FIGS. 2A and 2B show the effect of radiation in combination with TAXOL and L-PAM (Melphalan), respectively, in cervical carcinoma. Combination treatments were assessed for synergy using Chou Analysis and reported as the combination index (CI). A CI≦1.0 demonstrates synergy, a CI=1.0 demonstrates additivity, and a CI>1.0 demonstrates antagonism.
Figure 2B:
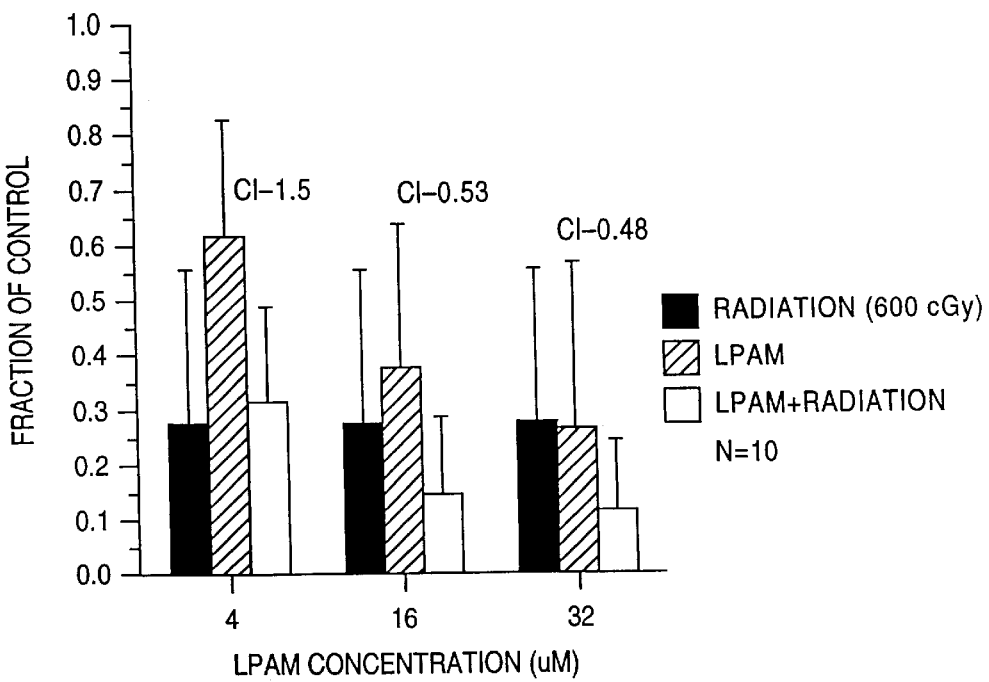
Figure 3A:
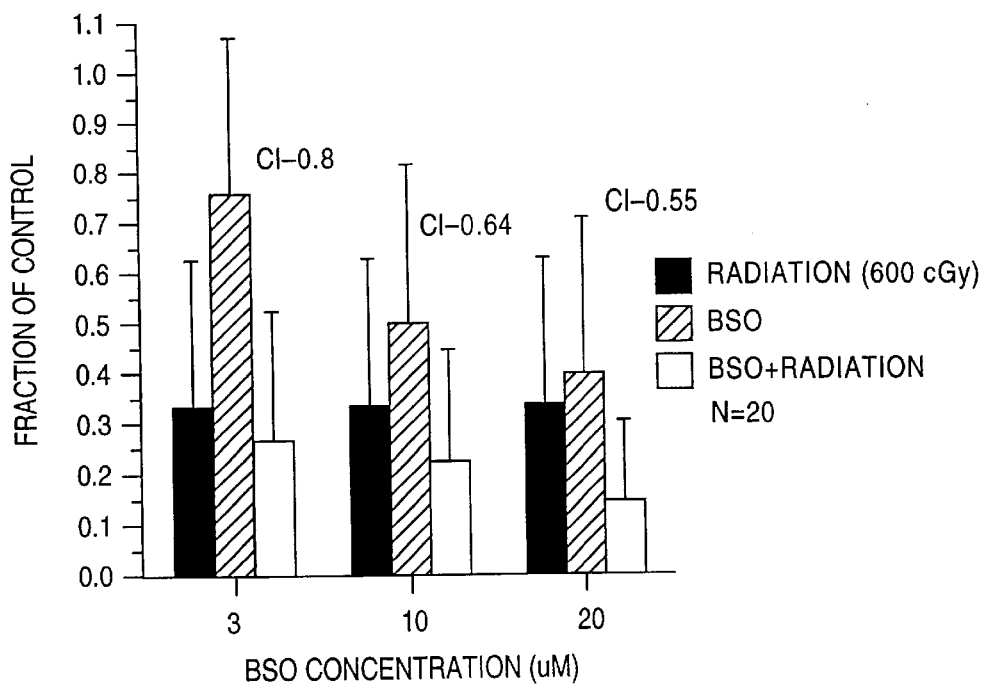
FIGS. 3A, 3B and 3C show the effect of radiation alone or in combination with buthionine sulfoximine (BSO) (3A), cisplatin (3B), or bis-dichloronitrosourea (BCNU) (3C) in cervical carcinoma. Cells were exposed to 600 cGY of radiation alone (red solid box), drug alone (green shaded box), or in combination (blue shaded box).
Figure 3B:
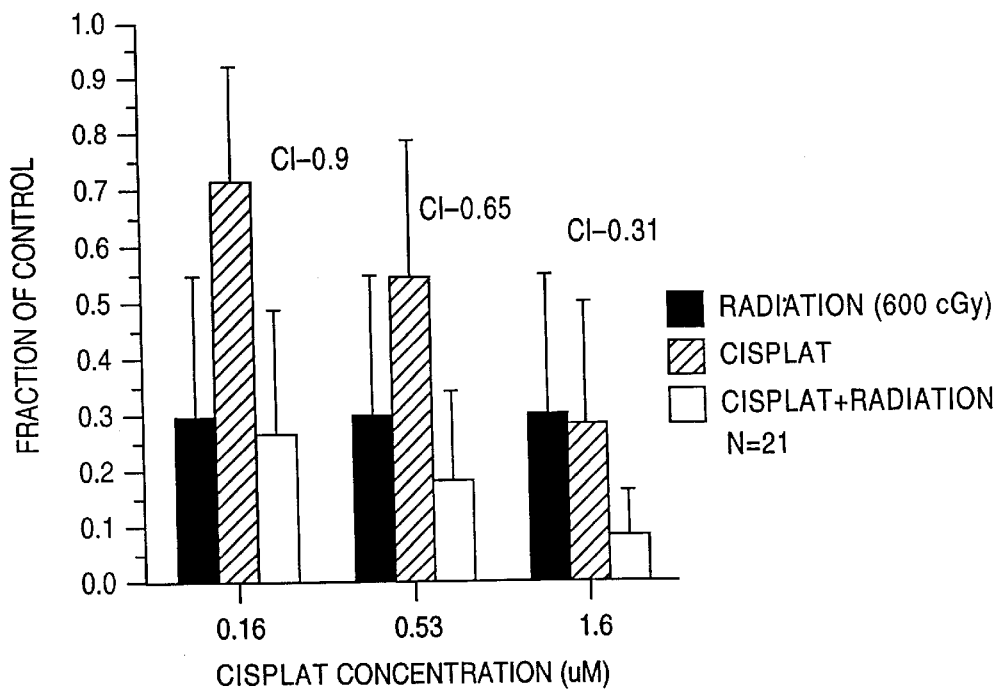
Figure 3C:
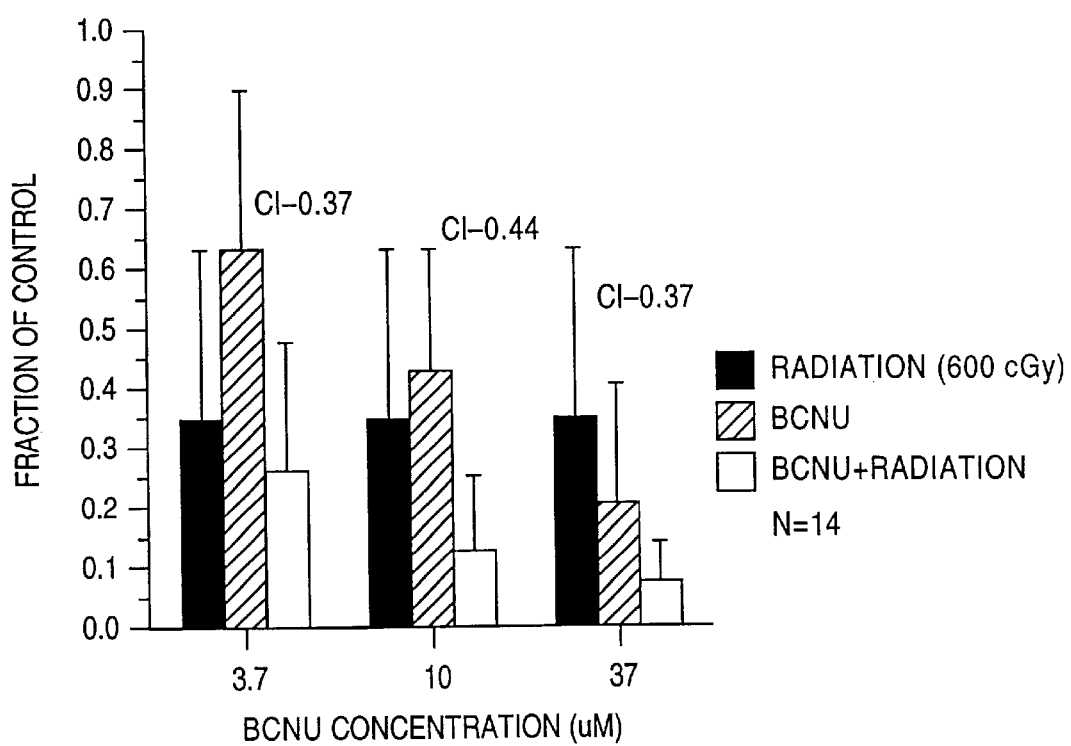

The present invention provides a fast, reliable method for predicting the radiosensitivity of tumor cells. In one aspect, the invention involves isolating and irradiating cancer cells and then incubating these cells with a labeled marker of cell proliferation, measuring the amount of labeled marker incorporated into the cells in order to determine the effect of radiation on the proliferation of cells, and then determining the relative resistance of the cells to radiation. In another aspect, radio-sensitizing or chemotherapeutic agents can be added to the assay prior to or after irradiation of the cells.

Definitions

As used herein, the term "cancer cells" refers to any cells which exhibit uncontrolled growth in a tissue or organ of a multicellular organism. The term "tumor" refers to an abnormal benign or malignant mass of tissue that is not inflammatory and possesses no physiological function.

"Irradiation" includes exposure to the action of electromagnetic radiation or alpha or beta particles, including, for example, x-rays, ultraviolet rays, alpha particles and gamma rays. The term "gray (Gy)" is the amount of radiation that will release one Joule in one kilogram of representative biological tissue. "Radiosensitivity" is used to refer to a cell which is readily affected by irradiation, for example, a sample which shows inhibited cell repair or decreased percentages of cells in the mitotic phase of cell growth after exposure to radiation. Likewise, the term "radiation resistance" refers to a cell which is not readily affected by irradiation and shows little or no change in cell repair or proliferation when exposed to radiation. "Radiosensitizing agents" include any agent which increases the sensitivity of cells to the effects of radiation therapy, usually by inhibiting cellular repair or by increasing the percentage of cells in the mitotic phases of cell growth. "Chemotherapeutic agents" include any chemicals used in the treatment or control of disease. Examples of cancer chemotherapeutics include, but are not limited to, cisplatin, carmustine (BCNU), and buthionine sulfoximine (BSO).

A "marker" indicative of cell proliferation includes any molecule whose presence or absence is correlated with an increase or decrease in cell growth or proliferation. For instance, radiolabeled nucleosides such as thymidine ($^3$H-thymidine) can be used as a marker to measure DNA synthesis, an indicator of cell proliferation. Accordingly, incorporation of $^3$H-Thymidine into cells is correlated with cell proliferation. Other markers which are indicative of cell proliferation are known to those of skill in the art and include, for example, nucleosides or nucleoside analogues.

A "label" is any compound or atom that is either attached to or incorporated into a macromolecule and is used to detect the presence of a compound, substance or macromolecule in a sample. Suitable labels, such as radioactive isotopes, are known to those of the skill in the art.

Thus, the present invention provides a fast, reliable method for assaying the radiation resistance of cancer cells. In one aspect, the invention includes isolating cancer cells from an individual, exposing the cells to radiation, incubating the radiation-exposed cells with a labeled marker indicative of cell proliferation, and measuring the amount of labeled marker. In one embodiment, the cancer cells are isolated from a cervical tumor biopsy. Standard surgical biopsy techniques may be used including, for example, the Loop Electrosurgical Excision Procedure (LEEP). In a preferred embodiment, the tumor specimens are non-necrotic, sterile and between 1.5 gram and 5 gram, more preferably between 1.5 and 3.0 grams. Tumor tissue is placed immediately into a sterile culture media tube, sealed and the tube labeled. Preferably, tumor tissue samples are processed within 24 hours of acquisition Samples are stored refrigerated, but not frozen.

Although the tissue samples can be used whole, it is preferred that the cancer cells isolated from a tumor be dissociated into cell suspensions by mechanical means and/or by enzymatic treatment such as DNAse and Collagenase Type 1. Mechanical dissociation and enzymatic treatment methods are known in the art and include, for example, mincing the tumor with sterile scissors and treatment with DNAse-free collagenase.

Cells may be assayed in any appropriate system. In one embodiment, multi-well tissue culture plates are prepared with double soft agar that comprises two layers of agar of different percentages. The bottom underlayer contains agar diluted in Solution E to a final percentage of 0.4%. Solution E consists of 75 mL heat activated fetal calf serum (FCS) filtered through a 0.2 micron vacuum filter, 500 mL Roswell Park Memorial Institute (RPMI) 1640 tissue culture medium (Gibco), 5.0 mL penicillin/streptomycin solution (10,000 units/mL penicillin, 10,000 μg/mL streptomycin) (Gibco), 5.0 mL L-glutamine (200 mM), and 2.5 mL Fungizone (0.125 μg/mL) (Gibco). This underlayer of agar prevents fibroblast from attaching to the plastic surface and allows only neoplastic cells to proliferate and supports the second and more dilute overlayer of agar that contains the tumor cells. The agar overlayer comprises agar diluted in Solution E to a final concentration of 0.12% and forms the three-dimensional matrix in which the tumor cells are exposed to irradiation and/or the chemotherapeutic drug(s) of interest.

The samples are maintained in any media useful in culturing cells. In the preferred embodiment, cells are plated in RPMI 1640 having 15% Fetal Calf Serum (FCS) and 0.3% agarose. Other suitable media will be known to those of skill in the art. It is preferred that the dissociated cells are transferred to the media in a specific concentration. The precise concentration of cancer cells per well will vary according to the nature of the labeled marker and the sensitivity of the label detection system. In a preferred embodiment, dissociated cancer cells are plated at between 1 to $5 \times 10^5$ cells per well.

After cells are plated in the multi-well plates with double soft agar, the plates are carefully placed onto the bed of the radiation source and aligned with the radiation beam apertures coordinates positioned beneath the bed. A plastic block of specific density is placed on top of the plates to facilitate proper and uniform radiation beam scatter and exposure to the cultured tumor cells. Radiation exposures of 1.5 Gy, and 6.0 Gy, for example, are administered to separate sets of the same tumor that have been pretreated with or without chemotherapeutic drug(s) (1 to 24 hours before radiation exposure, depending on the drug). The radiation source that is controlled by a computer is activated and calibrated to emit the appropriate level of radiation over a given time period. For higher radiation dosages, the radiation emission rates are adjusted for increased exposure. Equipment which produces irradiation is commercially available from various sources, and includes, for example, a linear accelerator (Varian Corp., Model 600C).

Cells are cultured after treatment for approximately three (3) days at 37° C. with 5% $CO_2$ atmosphere. Label is then added to the plates to determine the cellular response to treatment.

Labeled marker can be added directly to the cell culture media using sterile techniques. Useful labels include, but are not limited to, fluorescent markers or radioactive tags. The label is used in amounts sufficient to determine the amount of label incorporated into a cell. In a preferred embodiment, 100 μL of 5 μCi of $^3$H-Thymidine is added to each well containing cells and then incubated for approximately 2 days at 37° C. with 5% $CO_2$ atmosphere. Certain specimens comprising slow growing tumors such as breast or brain, or minimum yield samples or specimens being tested with 5-FU as the first drug (ie., colon or stomach tumor cells), are labeled again on day four of the assay and then harvested 48 hours after the second labeling. The thymidine incorporates into newly synthesized DNA, thereby providing an indication of the cell proliferative activity. Controls may also be included in each assay. A blank well indicates non-specific trapping of the $^3$H-Thymidine, while wells exposed to zero Gy radiation indicate full cell proliferation in tissue culture.

Incorporated labeled marker can then be separated from unincorporated labeled marker by any means known in the art. For instance, when using a label which incorporates into DNA, the DNA of the cancer cells can be isolated by any of the methods described in Sambrook et al. MOLECULAR CLONING: A LABORATORY MANUAL, 2d Ed., Cold Spring Harbor Press, 1989. Other useful methods of isolating labeled marker include precipitation, washing steps, column or paper chromatography, hybridization, immunoprecipitation, gel electrophoreses, and the like.

The amount of incorporated label is then measured. The appropriate method of measurement will depend on the nature of the label. Accordingly, for radioactive tags, the amount of radioactivity can be quantified using autoradiography, or, in a preferred embodiment, a liquid scintillation counter. For fluorescent labels, the amount of fluorescence can be measured using methods known in the art.

In another aspect, the invention provides for incubating the isolated cells with a radio-sensitizing or chemotherapeutic agent prior to or after irradiating the cells. In this way, any synergistic effects between radiation and chemical treatment can be measured.

In one embodiment, the cells are isolated and plated as described above, exposed to gamma radiation, and then radio-sensitizing chemotherapeutic agents are added. Preferably, the dose of radiosensitizing or chemotherapeutic agent encompasses the standard range of peak plasma levels achieved when the agent is given to an individual in a clinical setting. For example, cisplatin would be given in vitro at between 0.16 $\mu$M and 1.6 $\mu$M. The cells are then incubated with the radio-sensitizing or chemotherapeutic agent and, after three days, a labeled marker of cell proliferation, for example 5 $\mu$Ci of $^3$H-Thymidine, is added. The cells are incubated for 48 hours, the unincorporated labeled marker is removed, and the amount of marker measured.

In another aspect, the radio-sensitizing or chemotherapeutic agent is added prior to gamma irradiation. After irradiation with between 1.5 and 6.0 Gy, the cells are incubated for three days, labeled marker added, incubated for 48 hours and the amount of incorporated marker measured as described above.

It will be apparent to those skilled in the art that the method described herein is useful for assaying radiation sensitivity of any tumor cells.

All publications, patents and patent application disclosed herein are hereby incorporated by reference.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the radiation therapy and treatment art.

EXAMPLES

Example 1
In Vitro Radiation Response Assay for Cervical Carcinoma

Non-necrotic, sterile cervical cancer tumor specimens of between 1.5 and 3 grams (no more than 5 grams) were obtained by incisional biopsy after clinical staging but prior to initial treatment, ideally at the time of clinical staging examination under anesthesia The Loop Electrosurgical Excision Procedure (LEEP) is an accepted modality for tumor tissue acquisition.

Following incisional biopsy, tumor tissue was placed immediately into a sterile culture tube media. The tube was sealed and labeled in smudge-proof ink with the patient last name, first name, hospital record number and date of sample collection. The labeled tube was then placed into an outer protective tube, the outer tube sealed and enclosed in absorbent material for protection. Tumor tissue samples were stored under refrigeration (approximately 4° C.) and processed the next day.

Fresh Tumor Processing and In Vitro Treatment of Cell Suspensions

The tumor specimens were accessioned, weighed and a small representative section processed for paraffin block. A pathologist reviewed all tissue sections to confirm diagnosis. The remaining specimen (<10 g) was finely minced and incubated in approximately 20 mL of collagenase-enzyme solution for two hours at 37° C. at 5% $CO_2$ and stirred while incubated. The collagenase-enzyme solution consisted of 1.0 g/L collagenase type I and 0.1 g/L DNAse (2000 K units/mg) dissolved in RPMI media. 20 $\mu$L of antibiotic, typically gentamicin, was added to the specimen if bacteria were present. The cells were then washed and resuspended in fresh culture medium. Specimens containing clumps or strands of tissue after digestion with the enzyme solution are filtered through 200 micron mesh with the exception of breast specimens.

Viability was determined by tryphan blue exclusion as described in Shapiro, H. M., p. 129, PRACTICAL FLOW CYTOMETRY (Wiley-Liss, 2nd. ed., New York, 1988). A cytosin preparation of the cell suspension was examined for the presence of malignant cells and to determine the plating density. Multi-well tissue culture plates were prepared with double layer of soft agar as described above. Cancer cells were plated at 1 to 5×10$^5$ cells per well in assay media (RPMI 1640, 15% Fetal Calf Serum (FCS), 0.3% agarose). The Effect of Gamma Irradiation on Cervical Cancer Cells The wells of a 24-well tissue culture plate were filled with 0.5 mL of a bottom feeder layer of double soft agar comprising four (4) parts Solution E to one (1) part Agarose. The plate was then chilled for 15 minutes at 4° C. and then placed in an incubator. 50 $\mu$L of drug was added per well and each drug test per specimen was conducted in duplicate. Four negative control (no drug) and two positive control wells were included per plate. An agarose-cell suspension mixture was prepared by mixing two (2) parts of the agarose-Solution E mixture described above and one (1) part of a cell suspension diluted to a concentration of 1–5×10$^5$ cells/mL. 0.5 mL of this agarose-Solution E/cell suspension mixture was added to each well, while mixing gently to keep the cells in suspension. 1.5 mL of the remaining agarose-Solution E/cell suspension mixture was added to 1.0 mL of agarose solution and 1.5 mL agarose-Solution E mixture to serve as the half-cell control. This control mixture was added to appropriate wells in the tissue culture plate and then the plate was chilled for 15 minutes at 4° C. and then placed in an incubator at 37° C. at 5% $CO_2$.

Cell suspensions were exposed to gamma irradiation at three doses: 1.5, 3.0 and 6.0 Gy (0 Gy as negative control) in triplicate. Cell suspensions corresponding to each dose of irradiation were then exposed for 3 days to the radio-sensitizing chemotherapeutic agent with which the patient is being treated. For example, if the patient was receiving cisplatin, the in vitro cisplatin doses employed were 0.16 μM, 0.53 μM and 1.6 μM (0 μM as negative control), concentrations which encompass the standard range of peak plasma levels achieved clinically.

After three (3) days, 100 μL of a thymidine solution containing 5 μCi 3H-thymidine were added to each well and then the cells were incubated at least 48 hours before harvesting. Slow growing specimens such as breast or brain specimens or minimum yield samples or specimens being treated with 5-FU as the first drug (ie., colon or stomach tumors) were labeled again with $^3$H-thymidine 24 hours later and then harvested manually or by an automated cell harvester 48 hours after the second labeling. The amount of $^3$H-thymidine incorporated into the harvested cells contained in each well is determined by scintillation counting. Results obtained by these methods are shown in Table 2 below.

TABLE 2

In vitro radiation for cervical carcinoma to radiation, drug and their combination.

| Drug | N | FC, 6 Gy[1] | FC Drug[2] | FC Comb[3] | CI[4] |
|---|---|---|---|---|---|
| CPLAT 1.6 uM | 17 | 0.35 ± 0.28 | 0.26 ± 0.20 | 0.07 ± 0.08 | 0.30 |
| BCNU 10 uM | 13 | 0.35 ± 0.28 | 0.44 ± 0.20 | 0.13 ± 0.10 | 0.40 |
| BSO 20 uM | 15 | 0.35 ± 0.29 | 0.42 ± 0.30 | 0.15 ± 0.14 | 0.53 |
| L-PAM 16 uM | 8 | 0.33 ± 0.28 | 0.34 ± 0.25 | 0.16 ± 0.14 | 0.55 |
| TAXOL 1.2 uM | 12 | 0.34 ± 0.28 | 0.74 ± 0.25 | 0.21 ± 0.21 | 0.57 |

Fraction of control response = FC, combination index = CI and number of specimens tested = N.

Example 2
Comparison of Radiation Response in Cell Lines and Fresh Tumor Explants Five fresh tumor explants and four cell lines (C33A, SIHA, HT-3 and CASKI) were isolated and plated into assay media as described above. Cells were exposed to gamma irradiation (1.5, 3.0 or 6.0 Gy) with or without cisplatin (1.5 μM), carmustine (BCNU, 37 μM) or buthionine sulfoximine (BSO, 20 μM, known to deplete cellular glutathione). On day 3 of exposure to the chemotherapeutic agent, the cell suspensions treated as described above were labeled with 5 μCi $^3$H-thymidine. After 48 hours, the agarose-cell suspensions were melted with 1.0 mL of hot trichloroacetic acid and the precipitated radioactivity counted by liquid scintillation. Positive (200 mg/mL cisplatin-exposed) and negative (media-exposed) control cultures were performed with each assay. Cisplatin is added on Day 0 to the positive control wells to kill the cells. On Day 3, $^3$H-thymidine is added to the wells and, following harvesting of the cells, the radioactivity recorded in these wells served as the "background" control. Results, shown in Table 3, are reported as mean fraction of control (FC). For each combination of irradiation and drug, synergy was tested using Chou analysis, where a combination index (CI)<1 indicates synergistic interaction. In simple correlation analysis, an R value of>0.7 indicated cross-resistance.

TABLE 3

Irradiation Dose Dependent Proliferation Inhibition

| Drug | Target | FC 6.0 Gy (Radiation Alone) | FC Drug (Drug Alone) | FC Comb (Radiation + Drug) | CI | R |
|---|---|---|---|---|---|---|
| Cisplatin | Tumors* | 0.34 | 0.24 | 0.07 | 0.28 | 0.12 |
|  | Cell lines$ | 0.78 | 0.37 | 0.31 | 0.84 |  |
| BCNU | Tumors | 0.18 | 0.17 | 0.04 | 0.38 | 0.43 |
|  | Cell lines | 0.78 | 0.61 | 0.63 | 1.54 |  |
| BSO | Tumors | 0.34 | 0.23 | 0.05 | 0.37 | 0.76 |
|  | Cell lines | 0.78 | 0.88 | 0.83 | 2.00 |  |

*For all tumor data, n = 5
$For all cell line data, n = 4

These results demonstrate that fresh tumor explants were significantly more sensitive to irradiation than the cell lines. In addition, unlike the cell lines, fresh tumor cells consistently displayed synergy with combinations of irradiation and radiosensitizing drugs. The cross-resistance observed with BSO suggests that glutathione up-regulation is a common mechanism for both radiation and drug resistance.

What is claimed is:

1. A method for determining the resistance of cancer cells to radiation, the method comprising:

(a) isolating cancer cells from an individual;

(b) exposing the cells to a source of radiation;

(c) incubating the cells from step (b) with a labeled marker indicative of cell proliferation;

(d) measuring the amount of labeled marker incorporated into the cells in order to determine the effect of the radiation on the proliferation of the cells, and then (e) determining the relative resistance of the cells to the radiation;

wherein the cells are exposed to paclitaxel (Taxol) or melphalan (L-Pam) prior to step (b).

2. A method for determining the resistance of cancer cells to radiation, the method comprising:

(a) isolating cancer cells from an individual;

(b) exposing the cells to a source of radiation;

(c) incubating the cells from step (b) with a labeled marker indicative of cell proliferation;

(d) measuring the amount of labeled marker incorporated into the cells in order to determine the effect of the radiation on the proliferation of the cells, and then (e) determining the relative resistance of the cells to the radiation;

wherein the cells are exposed to paclitaxel (Taxol) or melphalan (L-Pam) after step (b).

* * * * *